United States Patent
Dyson et al.

(10) Patent No.: US 8,101,777 B2
(45) Date of Patent: Jan. 24, 2012

(54) IONIC LIQUIDS BASED ON IMIDAZOLIUM SALTS INCORPORATING A NITRILE FUNCTIONALITY

(75) Inventors: Paul Dyson, Ecublens (CH); Dongbin Zhao, Basel (CH); Zhaofu Fei, Reneus (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 1019 days.

(21) Appl. No.: 12/087,749

(22) PCT Filed: Aug. 25, 2004

(86) PCT No.: PCT/EP2004/009499
§ 371 (c)(1),
(2), (4) Date: Nov. 10, 2008

(87) PCT Pub. No.: WO2005/019185
PCT Pub. Date: Mar. 3, 2005

(65) Prior Publication Data
US 2009/0143597 A1 Jun. 4, 2009

Related U.S. Application Data

(60) Provisional application No. 60/497,776, filed on Aug. 26, 2003.

(51) Int. Cl.
C07D 233/56 (2006.01)
B01F 1/00 (2006.01)
C23G 5/00 (2006.01)

(52) U.S. Cl. .................................... 548/335.1; 252/364

(58) Field of Classification Search ............... 548/335.1; 252/364
See application file for complete search history.

(56) References Cited

FOREIGN PATENT DOCUMENTS

| FR | 8 357 M | 2/1971 |
|---|---|---|
| JP | 2000 191916 | 7/2000 |
| WO | 93/23402 | 11/1993 |
| WO | 02/053158 | 7/2002 |
| WO | 03/022812 | 3/2003 |
| WO | 2004/035542 | 4/2004 |

OTHER PUBLICATIONS

Zhao et al., Chem. Comm., 2004, 2500-2501.*

Wasserscheid P et al: "New, functionalised ionic liquids from Michael-type reactions—A chance for combinatorial ionic liquid development" Chemical Communications, No. 16, Jul. 3, 2003, pp. 2038-2039.
Wasserscheid P et al: "Ionic Liquids-New Solutions for Transition Metal Catalysis" Angewadte Chemie. International Edition, Verlag Chemie. Weinheim, DE, vol. 39, No. 21, Nov. 3, 2000 pp. 3773-3789.
Herrmann W A et al: "Heterocyclic Carbenes. 18, Chiral Oxazoline/Imidazoline-2-ylidene Complexes" Organometallics., vol. 17, No. 11, 1998, pp. 2162-2168.
Database Beilstein, Beilstein Institute for Organic Chemistry, Frankfurt-Main, DE: 1991, Database accession No. 4084291 (BRN) XP002308443.
Database Beilstein, Beilstein Institute for Organic Chemistry, Frankfurt-Main, DE; 1992, Database accession No. 5193589 (BRN) XP002308444.
Zhao D et al: "Synthesis and Characterization of Ionic Liquids Incorporating the Nitrile Functionality" Inorganic Chemistry, vol. 43, No. 6, Feb. 27, 2004, pp. 2197-2205.
Sasaki K et al: "A novel glycosidation of glycosyl fluoride using a designed ionic liquid and its effect on the stereoselectivity" Tetrahedron Letters., vol. 45, No. 38, Aug. 13, 2004, pp. 7043-7047, Nlelsevier Science Publishers, Amsterdam.

* cited by examiner

Primary Examiner — Robert Havlin
(74) Attorney, Agent, or Firm — Carmella A. O'Gorman

(57) ABSTRACT

Novel chemical compounds of the general formula $$K^+A^-,$$

in which $K^+$ is a 5- or 6-membered heterocyclic ring having 1-3 hetereo atoms, which can be independently N, S, or O; with the proviso that at least one of the hetereo atoms must be a quaternized nitrogen atom having a —R'CN substituent, wherein R' is alkyl ($C_1$ to $C_{12}$);
the heterocyclic ring having up to 4 or 5 substituents independently chosen from the moieties:
  (i) H;
  (ii) halogen or
  (iii) alkyl ($C_1$ to $C_{12}$), which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)_2$ or $C_nF_{(2n+1-x)}H_x$ where $1<n<6$ and $0<x<13$; and
  (iv) a phenyl ring which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_x)_2$ or $C_nF_{(2n+1-x)}H_x$ where $1<n<6$ and $0<x\leq13$; and
$A^-$ is any anion that provides a salt with a low melting point, below about 100° C.; A can be halide, $BF_4^-$, $PF_6^-$, $NO_3^-$, $CH_3CO_2^-$, $CF_3SO_3^-$, $(CF_3SO_2)_2N^-$, $(CF_3SO_2)_3C^-$, $CF_3CO_2^-$ or $N(CN)_{2-}$ or $[BF_3RCN]$
These compounds can be used as industrial solvents, especially as ligands for efficient catalyst recycling.

6 Claims, No Drawings

IONIC LIQUIDS BASED ON IMIDAZOLIUM SALTS INCORPORATING A NITRILE FUNCTIONALITY

This is a National Stage of International Application No. PCT/EP2004/009499 filed Aug. 25, 2004, which claims benefit of U.S. Provisional Application No. 60/497,776 filed Aug. 26, 2003, which in its entirety are herein incorporated by reference.

FIELD OF THE INVENTION

This invention relates to novel ionic liquids. The ionic liquids can be used as solvents to immobilize catalysts for the biphasic or multiphasic synthesis of chemical products such as pharmaceuticals.

BACKGROUND OF THE INVENTION

Ionic liquids are salts with a melting temperature below the boiling point of water. Ionic liquids useful as solvents in industrial applications are also liquids at room temperature.

Room temperature ionic liquids or molten salts were described for the first time in U.S. Pat. No. 2,446,331. The problem with these ionic liquids described in this patent is that the anionic component can decompose on contact with atmospheric moisture.

More recently, air and moisture stable ionic liquids have been prepared, and now extensive studies have been carried out in two main areas:
1. The development of new ionic liquids based on many different cation and anion combinations.
2. The application of ionic liquids as immobilizing media for lanthanide and actinide series and transition metal catalysts.

Ionic liquids are currently attracting considerable attention as novel solvents for organic synthesis and catalysis because the chemical industry is under pressure to replace environmentally damaging volatile organic solvents with more benign alternatives. "Room temperature ionic liquids", especially those based on 1,3-dialkylimidazolium cations, have emerged as leading contenders since they have negligible vapor pressure, are air and moisture stable, and are highly solvating for both ionic and molecular species, and as a result are suitable for multiphasic catalysis. Although applications in synthesis and catalysis have been most widely explored, with the first industrial scale process now on-line for over a year, ionic liquids are also finding uses in separation processes, in electrochemistry, as electrolytes in solar cells, as lubricants, and as matrices in MALDI mass spectrometry.

One of the attractive features of ionic liquids in synthesis and catalysis is that both the cationic and anionic components can be varied and modified, so that a liquid can be tailored to specific applications. The term "task-specific ionic liquids" has been used to describe low melting salts with functional groups, such as amine and amide, sulfonic acid, ether and alcohol, carboxylic, urea and thiourea and phosphine functionalities, as well as fluorous chains attached to the alkyl side chains. The definition of task-specific ionic liquids is also extended to include ionic liquids with functional anions such as carboranes, metal carbonyl anions such as [Co(CO)$_4$]$^-$; the proprietary catalyst [Rh(CO)$_2$I$_2$]$^-$ and alkylselenites.

If ionic liquids are to be used to immobilize catalysts in multiphasic reactions, then the design and synthesis of task-specific ionic liquids is extremely important. Many different reactions have been catalyzed using ionic liquids as immobilization solvents including hydrogenation, hydroformylation and C—C coupling reactions. While the non-nucleophilic nature of many ionic liquids seems to be advantageous, providing a protective environment for the catalyst which can extend its lifetime, it has also emerged that ionic liquids that incorporate a coordination centre might be extremely useful, such that the ionic liquid serves as both immobilization solvent and ligand to the catalyst. Wasserscheid et al first described this concept by introducing a diphenylphosphine group at the 2-position of an imidazolium cation; the resulting salt was a not a "room temperature ionic liquid" and had to be dissolved in another ionic liquid for effective use in biphasic catalysis. The ligand, by virtue of being a salt, is highly soluble in ionic liquids and is strongly retained during product extraction. Groups such as NH$_2$ and OH have also been successfully introduced into the imidazolium cation moieties but their ability to coordinate to lanthanide and actinide series and transition metals to give catalytically useful complexes is somewhat limited. More sophisticated functional groups such as thioureas and thioethers have been tethered to imidazolium based ionic liquids and they have been shown to extract toxic metal ions from aqueous solution.

It is one object of this invention to provide the synthesis and characterization of quaternized nitrogen-containing heterocyclic compounds, e.g. especially imidazolium or pyridinium heterocyclic compounds, such as salts, in which a nitrile group is attached to the alkyl side chain. The nitrile group is chosen as it is a promising donor to main group metals such as lithium and potassium, as well as lanthanide and actinide series and transition metals such as palladium and platinum. The physicochemical properties of these new ionic liquids are described. It is a further object of this invention to provide information about the relationship of the length of the alkyl unit linking the quaternized nitrogen-containing heterocyclic ring and the CN group, and how this relationship influences the melting point of the ionic liquid. Yet another object of this invention is to produce ionic liquids, which provide coordination centers (i.e. that act as ligands), while maintaining a low melting point, less than about 100° C., ideally at or below room temperature (i.e., acting as a solvent). A still further object of the invention is to demonstrate the applicability of these new ionic liquids in catalysis; as they have particular value in the immobilization of catalysts, enabling the catalyst to be recovered and efficiently recycled.

It is yet a further aspect of the invention to provide dual-functionalized ionic liquids and their properties.

DESCRIPTION AND SUMMARY OF THE INVENTION

Novel chemical compounds are provided of the general formula, $$K^+A^-,$$

in which K$^+$ is a 5- or 6-membered heterocyclic ring having 1-3 hetero atoms, which can be independently N, S, or O;
with the proviso that at least one of the hetero atoms must be a quaternized nitrogen atom having a —R' CN substituent, wherein R' is alkyl (C$_1$ to C$_{12}$);
the heterocyclic ring having up to 4 or 5 substituents independently chosen from the moieties:
(i) H;
(ii) halogen or
(iii) alkyl (C$_1$ to C$_{12}$), which is unsubstituted or partially or fully substituted by further groups, preferably F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$ or C$_n$F$_{(2n+1-x)}$H$_x$ where 1≤n≤6 and 0≤x≤13; and (iv) a phenyl ring which is unsubstituted or partially or fully substituted by further groups, preferably F, Cl, $N(C_nF_{(2n+1-x)}H_x)_2$, $O(C_nF_{(2n+1-x)}H_x)$, $SO_2(C_nF_{(2n+1-x)}H_{x2}$ or $C_nF_{(2n+1-x)}H_x$ where $1n<6$ and $0<x\leq13$; and $A^-$ is any anion that provides a salt with a low melting point, below about 100° C. Most preferably, A is halide, such as chloride, bromide, fluoride and the like; $BF_4^-$, $PF_6^-$, $NO_3^-$, $CH_3CO_2^-$, $CF_3SO_3^-$, $(CF_3SO_2)_2N^-$, $(CF_3SO_2)_3C^-$, $CF_3CO_2^-$ or $N(CN)_2^-$.

These compounds are useful in the immobilization of catalyst, especially lanthanide and actinide series and transition metal chlorides, such as palladium and platinum chlorides, to form complexes soluble in the ionic liquid. The catalysts can be recovered and recycled easily from the ionic liquids.

In the above compounds, the group R'C≡N where R' is an alkyl acts as the functional group and must always be present. More than one R'C≡N group may also be included, either attached to nitrogen or a carbon in the ring.

Particularly preferred as the K+ ring are the pyrrolium, pyrazolium, pyridinium, pyrazinium, pyrimidinium, imidazolium, thiazolium, oxazolium, and triazolium rings, some of which are illustrated in the series depicted below,

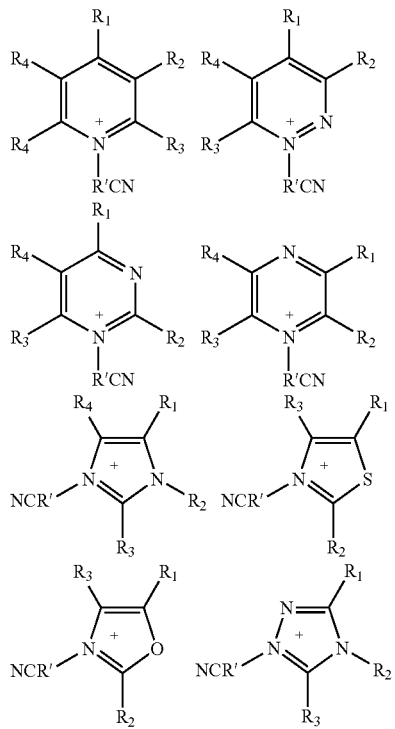

Most particularly preferred are the imidazolium and pyridinium rings. Essentially any combination of cation with one or more R'C≡N groups with any anion that results in a salt with a melting point below 100° C. is included.

In a further aspect the invention provides ionic liquids with a functionalized anion, in place of the usual anions which include $BF_4^-$, $PF_6^-$, $NO_3^-$, $CH_3CO_2^-$, $CF_3SO_3^-$, $(CF_3SO_2)_2N^-$, $(CF_3SO_2)_3C^-$, $CF_3CO_2^-$, $N(CN)_2^-$. The functionalized anion may be a nitrile functionalized anion, e.g. $[BF_3RCN]^-$ wherein R' is alkyl ($C_1$ to $C_{18}$, for example $C_1$ to $C_{12}$). Preferably the anion is $[BF_3CHCH_3CH_2CN]^-$.

How to Make the Ionic $K^{+A-}$ Liquids

The synthetic route to prepare the $K^+A^-$ salts utilizes as starting material the appropriate alkyl-substituted heterocyclic compound, which is then reacted with the appropriate chloroalkyl nitrile. The reactants are employed in approximately equimolar quantities, in a solvent which can be any of the usual solvent systems for heterocyclic chemistry, such as tetrahydofuran, acetonitrile, and diethyl ether. The reaction proceeds at ambient temperatures up to about 200° C.

The synthesis of e.g., 1-alkylnitrile-3-methylimidazolium and 1-alkylnitrile-2,3-dimethylimidazolium salts is depicted in Scheme 1, below. The imidazolium chlorides, e.g., [1-alkylnitrile-3-methylimidazolium][Cl], wherein alkyl is C=1-12, especially C=1-4, such as $(C_n=(CH_2)_n$, n=1 1a, n=2 2a, n=3 3a and n=4 4a) are prepared in high yield from 1-methylimidazole and the appropriate chloroalkyl nitrile $Cl(CH_2)_nCN$ in a modification to the literature procedure for the related 1-alkyl-3-methylimidazolium chlorides. The 1-alkylnitrile-2,3-dimethylimidazolium salt [1-akylnitrile-3-methylimidazolium]Cl 5a is prepared similarly from 1,2-dimethylimidazole and $Cl(CH_2)_3CN$. The synthesis of 1a has been described previously using an alternative a somewhat more complicated method. Both methods are found in the references: (a) Hitchcock, P. B.; Seddon, K. R.; Welton, T. *J. Chem. Soc. Dalton Trans.* 1993, 2639. (b) Suarez, P. A. Z.; Dullius, J. E. L.; Einloft, S.; de Souza, R. F.; Dupont, J. *Polyhedron* 1996, 15, 1217, and Herrmann, W. A.; Goossen, L. J.; Spiegler, M.; *Organometallics* 1998, 17, 2162.

The relatively strong electron withdrawing effect of the nitrile group activates chloromethylacetonitrile $ClCH_2CN$ to such an extent that it reacts smoothly with 1-methylimidazole in the absence of solvent to give 1a. However, as the alkyl chain in the chloroalkyl nitrile $Cl(CH_2)_nCN$ precursor increases in length, the temperature required to complete the reaction also increases.

Scheme 1

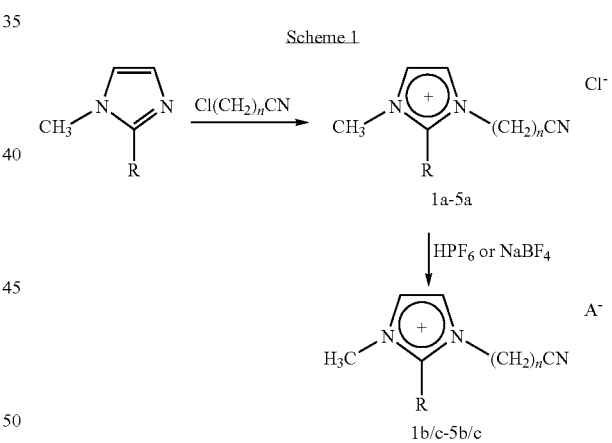

1a-5a

1b/c-5b/c

Scheme 1: Synthesis of ionic liquids: 1a n=1, R=H; 2a n=2, R=H; 3a n=3, R=H; 4a n=4,R=H; 5a n=3, R=$CH_3$; 1b n=1, R=H, A=$PF_6$; 1c n=1, R=H, A=$BF_4$; 2b n=2, R=H, A=$PF_6$; 2c n=2, R=H, A=$BF_4$; 3b n=3, R=H, A=$PF_6$; 3c n=3, R=H, A=$BF_4$; 4b n=4, R=H, A=$PF_6$; 4c n=4, R=H, A=$BF_4$; 5b n=3, R=$CH_3$, A=$PF_6$; 5c n=3, R=$CH_3$, A=$BF_4$.

Reaction of 1a-4a with a molecular equivalent of $HPF_6$ or $NaBF_4$ affords the imidazolium salts [1-alkylnitrile-3-methylimidazolium][$PF_6$] (n=1-4) 1b-4b and [1-alkylnitrile-3-methylimidazolium][$BF_4$] (n=1-4) 1c-4c, respectively. The imidazolium salts [1-alkylnitrile-3-methylimidazolium]$PF_6$ 5b and [1-alkylnitrile-3-methylimidazolium]$BF_4$ 5c are prepared from 5a using an analogous method. For 1b-5b the salts are washed with water in order to remove the hydrogen chloride formed during the anion exchange reaction, whereas tetrohydrofuran and diethyl ether are used to wash 1c-5c. The salts are then dried under vacuum for 1-2 days. The salts 2c, 3c, 4a, 4b and 3c are liquid at room temperature and are further purified by filtration through silica and left under vacuum at 40-50° C. for several days. All the imidazolium salts are obtained in medium to high yield. They are stable in air and show no signs of decomposition up to 150° C. Some of the ionic liquids within the scope of this invention are listed in the examples and appendix).

The synthetic route to prepare ionic liquids with a functionalized anion involves the preparation of the anion as a potassium salt, followed by anion metathesis with various imidazolium halides. The synthesis of e.g. K[BF$_3$CHCH$_3$CH$_2$CN]$^-$ is depicted in Scheme 2. The first step of the anion synthesis involves hydroboration of allyl cyanide using boron trichloride and triethylsilane, then addition of water to afford the boronic acid which is subsequently stirred with KHF$_2$ in ether/H$_2$O at ambient temperature. The product, K[BF$_3$CHCH$_3$CH$_2$CN]$^-$ 1, is recrystallized from acetone on addition of diethyl ether as colourless needles in 74% yield. Surprisingly alpha-alkene hydroboration affords boronic esters or acids at the alpha-position.

Commencing with 1-methylimidazole or 1-trimethylsylil-imidazole a series of imidazolium halides 2-10 were prepared. Subsequent metathesis with 1 in acetone give the dual-functionalized ionic liquids 11-19 in yield of 80 to 90%.

tion. If the catalyst and ionic liquid solution is to be used immediately in a catalyzed reaction, the amounts of the two can be those required for the reaction, the ionic liquid serving as solvent for the reaction step immediately following. The reaction product usually is separated from the reactants by solvent extraction, but the immobilized catalyst remains in the ionic liquid solvent, so is recovered and can be used for another reaction. The catalyst can also be prepared in a concentrated form in the ionic liquid, then later diluted with an excess of the ionic liquid to the desired catalyst concentration.

Since these complexes form part of the liquid, they are highly soluble in the ionic liquid. Many will catalyze a wide range of organic transformations, like hydrogenation, hydroformylation, metathesis, C—C coupling reactions, dimerization, oligomerization and polymerization.

The main advantages of the invention are:
1. The ionic liquids act as both ligand and solvent when used as media for organic synthesis in multiphasic catalysis, therefore, no other ligands are necessary.
2. The catalysts are strongly immobilized in the ionic liquids and can be easily recycled without loss (or minimal loss) of the catalyst.

The dual-functionalized ionic liquids are particularly advantageous due to their very low viscosities, e.g. as shown in Examples 33 to 35.

Scheme 2 Synthesis of 'dual-dunctionalised' ionic liquids with the [BF$_3$CHCH$_3$CH$_2$CN]$^-$anion.

Scheme 2

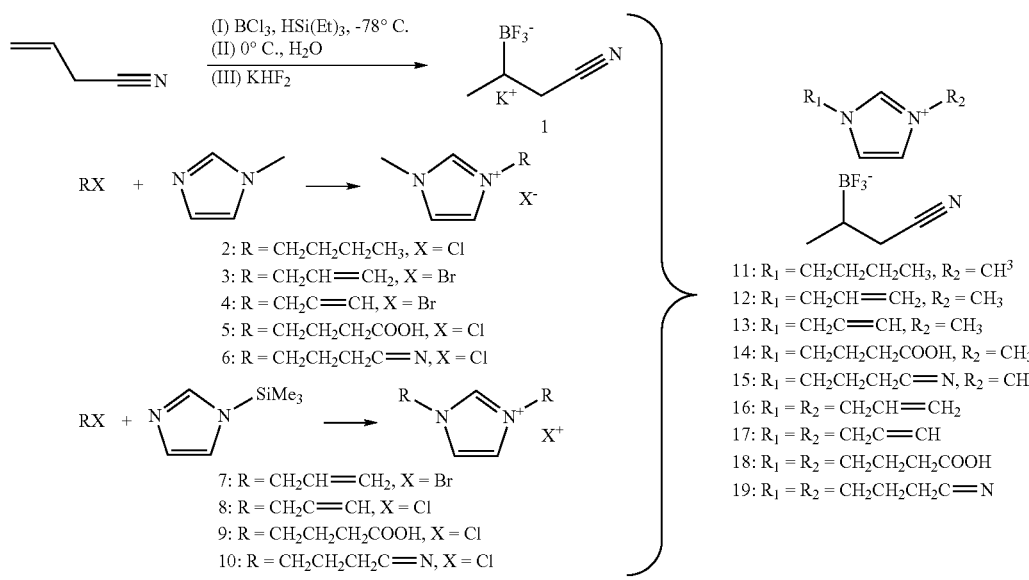

Uses of the Ionic Liquids

These ionic liquids can react with lanthanide and actinide series and transition metal chlorides and other metal salts or compounds used as catalysts to form complexes, for example, with PdCl$_2$, PtCl$_2$, RuCl$_3$, RhCl$_3$, and [Ru(arene)Cl$_2$]$_2$. Included within the term salts are not only the chlorides, but other salts which are known and employed to those skilled in the art. Metal containing molecular compounds used as catalysts, e.g. Wilkinson's catalyst and Grubb's catalyst, or the like can also be employed in this invention.

The process of making the complex is a straightforward one of dissolving a catalytically effective amount of the desired catalyst in enough of the ionic liquid to form a solu- As noted above, the nitrile derivatized ionic liquids of this invention are useful as solvents for multiphasic catalysis, in terms of catalyst retention and product separation. Dissolution of PdCl$_2$ in [C$_3$CNmim][BF$_4$] 3c affords [Pd(NCC$_3$mim)$_2$Cl$_2$]$_{[BF4]_2}$ in quantitative yield. The resulting solution is used to hydrogenate 1,3,-cyclohexadiene under biphasic conditions, which affords cyclohexene and cyclohexane. The overall conversion is 90% and the turnover frequency 247 molmol$^{-1}$h$^{-1}$; cyclohexene is formed with a selectivity of 97%. This is possibly because the monoene dissociates from the catalyst and is less soluble in the ionic liquid than the diene, which is therefore hydrogenated in preference. Hydrogenation reactions have been widely studied in ionic liquids, including the substrate 1,3-cyclohexadiene, but this would appear to be the first time selectivity to cyclohexene has been observed. Selective hydrogenation of 1,3-cyclohexadiene using palladium and platinum complexes with chiral ferrocenylamine sulfide and selenide ligands has been reported previously. It is clearly an advantage that the palladium ionic liquids system gives such selectivity without the need for additional co-ligands. However, the most important feature of this system is that the catalyst is part of the ionic liquid and therefore not easily lost during extraction of the product. No decrease in activity is observed after re-use of the catalyst solution. No palladium residues in the organic phase are detected using inductively coupled plasma analysis.

This invention is illustrated by the following examples.

EXAMPLES

The following examples are given to illustrate the synthesis of these ionic liquids and application in catalysis.

The 1-methylimidazole and 1,2-dimethylimidazole and chloronitriles are purchased from Fluka, $HPF_6$ and $NaBF_4$ are purchased from Aldrich and are used as received without further purification. The synthesis of the imidazolium salts 1a-5a is performed under an inert atmosphere of dry nitrogen using standard Schlenk techniques in solvents dried using the appropriate reagents and distilled prior to use. All other compounds are made without precautions to exclude air or moisture. IR spectra are recorded on a Perkin-Elmer FT-IR 2000 system. NMR spectra are measured on a Bruker DMX 400, using $SiMe_4$ for $^1H$, 85% $H_3PO_4$ for $^{31}P$, as external standards at 20° C. Electrospray ionization mass spectra (ESI-MS) are recorded on a ThermoFinnigan LCQ™ Deca XP Plus quadrupole ion trap instrument on sample diluted in methanol.[19] Samples are infused directly into the source at 5 μL min$^{-1}$ using a syringe pump and the spray voltage is set at 5 kV and the capillary temperature at 50° C. Samples 2c, 3c, 4a, 4b and 4c are purified by filtration through silica and left under vacuum (ca. 0.1 mm Hg) at 40-50° C. in order to remove traces of salt impurities and volatile components. Differential scanning calorimetry is performed with a SETARAM DSC 131. Density is determined with a picometer at room temperature (20±1° C.) on 1.0 ml of sample. The measurements are repeated three times and average values are used. Viscosities are measured with a Brookfield DV-II+ viscometer on 0.50 ml of sample. The temperature of the samples is maintained to 25±1° C. by means of an external temperature controller. The measurements are performed in duplicate.

Example 1

Synthesis of [1-methylnitrile-3-methylimidazolium]Cl 1a

A mixture of 1-methylimidazole (8.21 g, 0.10 mol) and $ClCH_2CN$ (9.06 g, 0.12 mol) is stirred at room temperature for 24 hours, during which time the reaction mixture turned to a solid. The solid is washed with diethyl ether (3×30 ml) and dried under vacuum for 24 hours, yield: 14.5 g, 92%; M.p. 170° C. Crystals suitable for X-ray diffraction are obtained by slow diffusion of ethyl ether into an acetonitrile solution of the compound at room temperature. ESI-MS ($CH_3OH$): positive ion: 122 [CCNmim], negative ion: 35 [Cl]. $^1H$ NMR ($D_2O$): δ=9.06 (s, 1H), 7.72 (s, 1H), 7.61 (s, 1H), 4.65 (s, 2H), 3.96 (s, 3H). $^{13}C$ NMR ($D_2O$): δ=140.40, 127.65, 125.52, 117.02, 74.82, 39.54. IR (cm$^{-1}$): 3177, 3126, 3033 ($v_{C-H}$ aromatic), 2979, 2909, 2838, 2771 ($v_{C-H}$ aliphatic), 2261 ($v_{C≡N}$), 1769 ($v_{C=N}$). Anal. Calcd for $C_6H_8ClN_3$ (%): C, 45.73, H, 5.12, N, 22.66; Found: C, 45.86, H, 5.26, N, 22.58.

Example 2

Synthesis of [1-methylnitrile-3-methylimidazolium]$PF_6$ 1b

To a solution of 1a (4.73 g, 0.03 mol) in water (50 ml), $HPF_6$ (8.03 g, 60 wt %, 0.033 mol) is added at room temperature. After 10 minutes the solid that had formed is collected by filtration and washed with ice-water (3×15 ml) and then dried under vacuum. Yield: 5.61 g, 70%; M.p. 78° C. ESI-MS ($CH_3OH$): positive ion: 122 [CCNmim], negative ion: 145 [$PF_6$]. $^1H$ NMR ($CD_3CN$): δ=8.59 (s, 1H), 7.53 (s, 1H), 7.44 (s, 1H), 5.41 (s, 2H), 3.86 (s, 3H). $^{13}C$ NMR ($CD_3CN$): δ=139.9, 127.6, 125.5, 120.5, 40.0, 39.3.3. $^{31}P$ NMR ($CD_3CN$): −145.25 (hept). IR (cm$^{-1}$): 3180, 3133, 3027 ($v_{C-H}$ aromatic), 2983, 2938 ($v_{C-H}$ aliphatic), 2274 ($v_{C≡N}$), 1602 ($v_{C=N}$). Anal. Calcd for $C_6H_8N_3F_6P$ (%): C, 26.98, H, 3.02, N, 15.73; Found: C, 27.02, H, 3.09, N, 15.66.

Example 3

Synthesis of [1-methylnitrile-3-methylimidazolium]$BF_4$ 1c

A mixture of 1a (4.73 g, 0.03 mol) and $NaBF_4$ (3.62 g, 0.033 mol) in acetone (80 ml) is stirred at room temperature for 48 hours. After filtration and removal of the solvents the resulting pale yellow waxy solid is washed with tetrohydrofuran and diethyl ether to give the product. Yield: 5.76 g, 92%; M.p. 35° C. ESI-MS ($CH_3OH$): positive ion: 122 [CCNmim], negative ion: 87 [$BF_4$]. $^1H$ NMR ($CD_3CN$): δ=8.67 (s, 1H), 7.56 (s, 1H), 7.47 (s, 1H), 5.26 (s, 2H), 3.87 (s, 3H). $^{13}C$ NMR ($CDCl_3$): δ=140.35, 127.57, 125.46, 116.76, 39.79, 39.21. IR (cm$^{-1}$): 3171, 3124, 3015 ($v_{C-H}$ aromatic), 2977, 2845 ($v_{C-H}$ aliphatic), 2253 ($v_{C≡N}$), 1588 ($v_{C=N}$). Anal. Calcd for $C_6H_8BF_4N_3$(%): C, 34.48, H, 3.86, N, 20.11; Found: C, 34.52, H, 3.82, N, 20.26.

Example 4

Synthesis of [1-ethylnitrile-3-methylimidazolium]Cl 2a

A mixture of 1-methylimidazole (8.21 g, 0.10 mmol) and $Cl(CH_2)_2CN$ (10.74 g, 0.12 mol) is stirred in toluene (20 ml) at 70° C. for 24 hours. The resulting white solid is washed with diethyl ether (5×30 ml). The product is then dried in vacuum for 24 hours. Yield: 15.5 g, 82%; M.p. 50° C. ESI-MS ($CH_3OH$): Positive ion: 136 [$C_2$CNmim], negative ion: 35 [Cl]. $^1H$ NMR ($D_2O$): δ=8.73 (s, 1H), 7.48 (s, 1H), 7.46 (s, 1H), 4.64 (t, J(H, H)=6.8 Hz, 2H), 3.94 (s, 3H), 3.03 (t, J(H, H)=6.8 Hz, 2H); $^{13}C$ NMR ($D_2O$): δ=139.58, 138.05, 126.16, 122.53, 47.86, 42.12, 38.83. IR (cm$^{-1}$): 3244 ($v_{C-H}$ aromatic), 2916, 2788, 2700 ($v_{C-H}$ aliphatic), 2250 ($v_{C≡N}$), 1720 ($v_{C=N}$). Anal. Calcd for $C_7H_{10}ClN_3$ (%): C, 48.99, H, 5.87, N, 24.48; Found: C, 50.02, H, 5.75, N, 24.71.

Example 5

Synthesis of [1-ethylnitrile-3-methylimidazolium]$PF_6$ 2b

The same procedure is followed as that described above for 1b, except 2a (5.15 g, 0.03 mol) and $HPF_6$ (8.03 g, 60 wt %, 0.033 mol) are used, and the product is obtained as a white solid. Yield: 6.83 g, 81%; M.p. 35° C. ESI-MS (CH$_3$OH): Positive ion: 136 [C$_2$CNmim], negative ion: 145 [PF$_6$]. $^1$H NMR (CD$_3$CN): δ=8.64 (s, 1H) 7.50 (s, 1H), 7.43 (s, 1H), 4.46 (t, J(H, H)=6.49 Hz, 2H), 3.89 (s, 3H), 3.03 (t, J(H, H)=6.49 Hz, 2H). $^{13}$C NMR (CD$_3$CN): δ=139.36, 127.13, 125.34, 120.49, 47.87, 39.01, 21.92. $^{31}$P NMR (CD$_3$CN): −142.90 (hept). IR (cm$^{-1}$): 3168, 3126, 3101 ($v_{C-H}$ aromatic), 2964 ($v_{C-H}$ aliphatic), 2255 ($v_{C\equiv N}$), 1704 ($v_{C=N}$). Anal. Calcd for C$_7$H$_{10}$F$_6$N$_3$P (%): C, 29.90, H, 3.58, N, 14.95; Found: C, 29.95, H, 3.62, N, 14.88.

Example 6

Synthesis of [1-ethyinitrile-3-methylimidazolium]BF$_4$ 2c

The same procedure is followed as that described above for 1c, except 2a (5.15 g, 0.03 mol) is used instead of 1a. The product is obtained as pale yellow liquid at room temperature. Yield: 5.69 g, 85%; M.p. 20° C. ESI-MS (CH$_3$OH): Positive ion: 136 [C$_2$CNmim], negative ion: 87 [BF$_4$]. $^1$H NMR (CD$_3$CN,): δ=8.56 (s, 1H), 7.41 (s, 1H), 7.37 (s, 1H), 4.48 (brs, 2H), 3.88 (s, 3H), 3.05 (brs, 2H). $^{13}$C NMR (CD$_3$CN): δ=138.33, 126.22, 122.56, 121.04, 47.81, 38.54, 21.81. IR (cm$^{-1}$): 3165 and 3124 ($v_{C-H}$ aromatic), 2955 and 2855 ($v_{C-H}$ aliphatic), 2251 ($v_{C\equiv N}$), 1736 ($v_{C=N}$). Anal. Calcd for C$_7$H$_{10}$N$_3$BF$_4$ (%): C, 37.70, H, 4.52, N, 18.84; Found: C, 37.52, H, 4.65, N, 19.05.

Example 7

Synthesis of 1[-propylnitrile-3-methylimidazolium]Cl 3a

A mixture of 1-methylimidazole (8.21 g, 0.10 mmol) and Cl(CH$_2$)$_3$CN (12.43 g, 0.12 mol) is stirred at 80° C. for 24 hours. The resulting white solid is washed with diethyl ether (3×30 ml). The product is dried in vacuum for 24 hours. Yield: 17.6 g, 95%; M.p. 80° C. ESI-MS (CH$_3$OH): Positive ion: 150 [C$_3$CNmim], negative ion: 35 [Cl]. $^1$H NMR (CDCl$_3$): δ=8.73 (s, 1H), 7.45 (s, 1H), 7.39 (s, 1H), 4.27 (t, J(H, H)=6.8 Hz, 2H), 3.82 (s, 3H), 2.50 (t, J(H, H)=6.8 Hz, 2H), 2.20 (t, J(H, H)=6.8 Hz, 2H). $^{13}$C NMR (CDCl$_3$): δ=134.11, 130.49, 120.01, 116.19, 44.01, 30.87, 21.21, 9.87. IR (cm$^{-1}$): 3373, 3244, 3055 ($v_{C-H}$ aromatic), 3029, 2974, 2949, 2927 ($v_{C-H}$ aliphatic), 2243 ($v_{C\equiv N}$), 1692 ($v_{C=N}$). Anal. Calcd for C$_8$H$_{12}$ClN$_3$ (%): C, 51.76, H, 6.51, N, 22.63; Found: C, 51.72, H, 6.55, N, 22.71.

Example 8

Synthesis of [1-propylnitrile-3-methylimidazolium]PF$_6$ 3b

The same procedure is followed as that described above for 1b, except 3a (5.57 g, 0.03 mol) is used instead of 1a. The product is obtained as white solid. Yield: 6.90 g, 78%; M.p. 75° C. ESI-MS (CH$_3$OH): Positive ion: 150 [C$_3$CNmim], negative ion: 145 [PF$_6$]. $^1$H NMR (CDCl$_3$): δ=8.63 (s, 1H), 7.59 (s, 1H), 7.55 (s, 1H), 4.42 (t, J(H, H)=7.0 Hz, 2H), 4.03 (s, 3H), 2.66 (t, J(H, H)=7.0 Hz, 2H), 2.33 (m, 2H). $^{13}$C NMR (CDCl$_3$): δ=135.50, 131.80, 120.10, 116.50, 44.25, 33.30, 22.50, 9.98. $^{31}$P NMR (CDCl$_3$): −145.90 (hept). IR (cm$^-$): 3171, 3158, 3128 ($v_{C-H}$ aromatic), 2980, 2807 ($v_{C-H}$ aliphatic), 2246 ($v_{C\equiv N}$), 1696 (($v_{C=N}$). Anal. Calcd for C$_8$H$_{12}$F$_6$N$_3$P (%): C, 32.55, H, 4.10, N, 14.24; Found: C, 32.59, H, 4.11, N, 14.30.

Example 9

Synthesis of [1-propylnitrile-3-methylimidazolium]BF$_4$ 3c

The same procedure is followed as that described above for 1c, except 3a (5.57 g, 0.03 mol) is used instead of 1a. Yield: 6.4 g, 90%; M. p. −71.9° C. ESI-MS (CH$_3$OH): Positive ion: 150 [C$_3$CNmim], negative ion: 87 [BF$_4$]. $^1$H NMR (CDCl$_3$): δ=9.32 (s, 1H), 8.18 (s, 1H), 8.14 (s, 1H), 4.96 (brs, 2H), 4.54 (s, 3H), 3.20 (brs, 2H), 2.85 (brs, 2H). $^{13}$C NMR (CDCl$_3$): δ=135.03, 131.17, 120.69, 116.71, 44.69, 33.78, 22.01, 10.15. IR (cm$^{-1}$): 3161, 3121 ($v_{C-H}$ aromatic), 2971 ($v_{C-H}$ aliphatic), 2249 ($v_{C\equiv N}$), 1712 ($v_{C=N}$). Anal. Calcd for C$_8$F$_4$BH$_{12}$N$_3$ (%): C, 40.54, H, 5.10, N, 17.73; Found: C, 40.58, H, 5.13, N, 17.69.

Example 10

Synthesis of [1-butylnitrile-3-methylimidazolium]Cl 4a

A mixture of 1-methylimidazole (8.21 g, 0.10 mmol) and Cl(CH$_2$)$_4$CN (14.1 g, 0.12 mol) is stirred at 80° C. for 4 hours. The temperature is then increased to 110° C. and the reaction mixture is stirred at for further 2 hours. After cooling, the reaction mixture is washed with diethyl ether (3×15 ml) and dried under vacuum for 24 hours. The product is obtained as viscous brownish liquid. Yield: 17.9 g, 90%; M.p. 32° C. ESI-MS (CH$_3$OH): Positive ion: 164 [C$_4$CNmim], negative ion: 35 [Cl]. $^1$H NMR (CD$_3$CN): δ=9.99 (s, 1H), 7.75 (s, 1H), 7.70 (s, 1H), 4.41 (t, J(H, H)=7.2 Hz, 2H), 3.94 (s, 3H), 2.57 (t, J(H, H)=7.0 Hz, 2H), 2.07 (m, J(H, H)=6.8 Hz, 2H), 1.64 (m, J(H, H)=6.8 Hz, 2H). $^{13}$C NMR (CD$_3$CN): δ=134.22, 129.29, 127.97, 125.81, 123.18, 41.50, 34.43, 27.47, 21.77. IR (cm$^{-1}$): 3138, 3088, 3082 ($v_{C-H}$ aromatic), 2948 ($v_{C-H}$ aliphatic), 2241 ($v_{C\equiv N}$), 1701 (($v_{C=N}$). Anal. Calcd for C$_9$H$_{14}$ClN$_3$ (%): C, 54.13, H, 7.07, N, 21.04; Found: C, 54.21, H, 7.09, N, 21.09.

Example 11

Synthesis of [1-butylnitrile-3-methylimidazolium]PF$_6$ 4b

The same procedure is followed as that described above for 1b, except 4a (5.99 g, 0.03 mol) is used instead of 1a. The product is obtained as brown liquid at room temperature. Yield: 7.6 g, 82%; M.p. −60.3° C. ESI-MS (CH$_3$OH): positive ion: 164 [C$_3$CNmim], negative ion: 145 [PF$_6$]. $^1$H NMR (CD$_3$CN): δ=8.45 (s, 1H), 7.38 (s, 1H), 7.35 (s, 1H), 4.15 (t, J(H, H)=7.17 Hz, 2H), 3.83 (s, 3H), 2.44 (t, J(H, H)=7.17 Hz, 2H), 1.93 (m, J(H, H)=7.17 Hz, 2H), 1.64 (m, J(H, H)=7.17 Hz, 2H). $^{13}$C NMR (CD$_3$CN): δ=138.95, 126.72, 125.16, 122.85, 120.80, 38.78, 31.61, 24.74, 18.93. $^{31}$P NMR (CDCl$_3$): −140.80 (hept). IR (cm$^{-1}$): 3168, 3123 ($v_{C-H}$ aromatic), 2972, 2901 ($v_{C-H}$ aliphatic), 2250 ($V_{C\equiv N}$), 1577 (($v_{C=N}$). Anal. Calcd for C$_9$F$_6$H$_{14}$N$_3$P (%): C, 34.96, H, 4.56, N, 13.59; Found: C, 35.05, H, 4.41, N, 13.64.

Example 12

Synthesis of [1-butylnitrile-3-methylimidazolium]BF$_4$ 4c

The same procedure is followed as that described above for 1c, except 4a (5.99 g, 0.03 mol) is used instead of 1a. The product is obtained as brown liquid at room temperature. Yield: 6.4 g, 85%; M.p. −71.9° C. ESI-MS (CH$_3$OH): Positive ion: 164 [C$_3$CNmim], negative ion: 87 [BF$_4$]. $^1$H NMR (CD$_3$CN): δ=8.54 (s, 1H), 7.43 (s, 1H), 7.39 (s, 1H), 4.17 (brs, 2H), 3.83 (s, 3H), 2.44 (brs, 2H), 1.92 (brs, 2H), 1.60 (brs, 2H). $^{13}$C NMR (CD$_3$CN): δ=139.24, 131.19, 128.02, 126.68, 123.72, 38.69, 31.64, 24.70, 18.64. IR (cm$^{-1}$); 3161, 3120 ($v_{C-H}$ aromatic), 2955, 2876 ($v_{C-H}$ aliphatic), 2247 ($v_{C≡N}$). 1575 ($v_{C=N}$). Anal. Calcd for C$_9$H$_{14}$N$_3$BF$_4$ (%): C, 43.06, H, 5.62, N, 16.74; Found: C, 43.12, H, 5.53, N, 16.70.

Example 13

Synthesis of [1-methylnitrile-2,3-dimethylimidazolium]Cl 5a

A mixture of 1,2-dimethylimidazole (9.61 g, 0.10 mol) and Cl(CH$_2$)$_3$CN (12.43 g, 0.12 mol) is stirred at 100° C. for 24 hours. Two phases are formed at the end of the reaction. The upper phase is decanted and the lower phase is washed with diethyl ether (3×30 ml). A pale yellow solid is formed during the washing and the product is dried in vacuum for 24 hours at room temperature. Yield: 18.6 g, 93%; M.p. 105° C. ×(CH$_3$OH): Positive ion: 164 [C$_3$CNdimim], negative ion: 35 [Cl]. $^1$H NMR (CD$_3$CN): δ=7.50 (s, 1H), 7.31 (s, 1H), 4.14 (t, J(H, H)=7.17 Hz, 2H), 3.71 (s, 3H), 2.53 (s, 3H), 2.46 (t, J(H, H)=7.17 Hz, 2H), 2.11 (m, J(H, H)=7.17 Hz, 2H). $^{13}$C NMR (CD$_3$CN): δ=125.52, 123.70, 122.32, 120.73, 49.47, 37.66, 28.12, 16.50, 11.92. IR (cm$^{-1}$): 3182, 3098, 3046 ($v_{C-H}$ aromatic), 2989, 2898, 2834 ($v_{C-H}$ aliphatic), 2240 ($v_{C≡N}$), 1631 ($v_{C=N}$). Anal. Calcd for C$_9$H$_{14}$ClN$_3$ (%): C, 54.13, H, 7.07, N, 21.04; Found: C, 54.18, H, 7.17, N, 20.92.

Example 14

Synthesis of [1-methylnitrile-2,3-dimethylimidazolium]PF$_6$ 5b

The same procedure is followed as that described above for 1b, except 5a (5.99 g, 0.03 mol) is used instead of 1a. The product is obtained as white solid at room temperature. Yield: 7.33 g, 79%; M.p. 85° C. ESI-MS (CH$_3$OH): Positive ion: 164 [C$_3$CNdimim], negative ion: 145 [PF$_6$]. $^1$H NMR (CD$_3$CN): δ=7.34 (s, 1H), 7.32 (s, 1H), 4.18 (t, J(H, H)=7.17 Hz, 2H), 3.75 (s, 3H), 2.55 (s, 3H), 2.51 (t, J(H, H)=7.17 Hz, 2H), 2.14 (m, J(H, H)=7.17, 2H). $^{13}$C NMR (CD$_3$CN): δ=144.91, 122.87, 120.99, 120.59, 46.85, 35.08, 25.02, 14.09, 9.37. $^{31}$P NMR (CD$_3$CN): −140.80 (hept). IR (cm$^{-1}$): 3150 ($v_{C-H}$ aromatic), 2966 ($v_{C-H}$ aliphatic), 2249 ($v_{C≡N}$), 1628 ($v_{C=N}$). Anal. Calcd for C$_9$F$_6$H$_{14}$N$_3$P (%): C, 34.96, H, 4.56, N, 13.59; Found: C, 35.02, H, 4.52, N, 13.61.

Example 15

Synthesis of [1-methylnitrile-2,3-dimethylimidazolium]BF$_4$ 5c

The same procedure is followed as that described above for 1c, except 5a (5.99 g, 0.03 mol) is used instead of 1a. The product is obtained as white waxy solid at room temperature. Yield: 6.77 g, 90%; M.p. 40° C. ESI-MS (CH$_3$OH): Positive ion: 164 [C$_3$CNdimim], negative ion: 87 [BF$_4$]. $^1$H NMR (CD$_3$CN): δ=7.31 (s, 1H), 7.30 (s, 1H), 4.15 (t, J(H, H)=6.84 Hz, 2H), 3.72 (s, 3H), 2.59 (s, 3H), 2.47 (t, J(H, H)=6.84 Hz, 2H), 2.13 (m, J(H, H)=6.84, 2H). $^{13}$C NMR (CD$_3$CN): δ=125.54, 123.70, 122.08, 120.52, 49.51, 37.71, 28.04, 16.59, 11.98. IR (cm$^{-1}$) 3185, 3145 ($v_{C-H}$ aromatic), 2966 ($v_{C-H}$ aliphatic), 2244 ($v_{C≡N}$), 1701 (($v_{C=N}$). Anal. Calcd for C$_9$H$_{14}$BF$_4$N$_3$ (%): C, 43.06, H, 5.62, N, 16.74; Found: C, 42.85, H, 5.75, N, 16.68.

Example 16

Synthesis of [Pd(1-methylnitrile-2,3-dimethylimidazolium)$_2$Cl$_2$][BF$_4$]$_2$ A mixture of 5c (153 mg, 0.61 mmol) and palladium chloride (54 mg, 0.305 mmol) in 5.0 ml dichloromethane is stirred at room temperature for 3 days. The resulting yellow solid is extracted by filtration, washed with diethyl ether (2×5.0 ml) and dried in vacuum. Yield: 195 mg, 94%; M.p.: 130° C.; $^1$H NMR (DMSO): δ=7.62 (s, 1H), 7.61 (s, 1H), 4.16 (t, J(H, H)=7.17 Hz, 2H), 3.72 (s, 3H), 2.57 (s, 3H), 2.56 (brs, 3H), 2.06 (m, J(H, H)=7.17 Hz, 2H); $^{13}$C NMR (DMSO): δ=148.10, 125.91, 124.20, 123.16, 49.61, 38.09, 28.39, 16.81 and 12.60; Anal. Calcd for C$_{18}$H$_{28}$B$_2$Cl$_2$F$_8$N$_6$Pd (%): C, 31.82, H, 4.15, N, 12.37; Found: C, 31.75, H, 4.10, N, 12.34; IR (cm$^{-1}$): 3152 and 3120 ($v_{C-H}$ aromatic), 2988, 2973 and 2901 ($v_{C-H}$ aliphatic), 2325 ($v_{C≡N}$), 1692 (($v_{C=N}$).

Example 17

Synthesis of [1-cyanopropyl-3-methylimidazolum]$_2$[PdCl$_4$]

A reaction mixture of PdCl$_2$ (177 mg, 1.0 mmol) and 3a (377 mg, 2.00 mmol) in dichloromethane (2 ml) is stirred at r.t. for 4 days. The resulting orange solid is collected by centrifugation and washed with dichloromethane (20 ml). Drying in vacuum gave the product in pure form. Yield: 548 mg, 100%. Mp: 178° C. $^1$H NMR (DMSO-d$_6$): 2.18 (t, 2H), 2.64 (t, 2H), 3.89 (s, 3H), 4.32 (t, 2H), 7.79 (s, 1H), 7.87 (s, 1H), 9.37 (s, 1H). $^{13}$C NMR (DMSO-d$_6$): 135.28, 131.36, 120.13, 116.18, 44.02, 31.22, 21.77, 9.99. Microanalysis: Found (Calc.): C, 35.03 (35.07), H, 4.41 (4.44), N, 15.32 (15.29)%. IR (cm$^{-1}$): U$_{CN}$, 2241(s). The compound could be dissolved in ionic liquids and used as a catalyst, the results in the hydrogenation of 1,3-cyclohexadiene are similar to those obtained in EXAMPLE 19.

Example 18

Synthesis of [(1-cyanopropyl-3-methylimidazolum)$_2$PdCl2][BF$_4$]$_2$

A reaction mixture of PdCl$_2$ (177 mg, 1.0 mmol) and (474 mg, 2.00 mmol) [C$_3$CNmim][BF$_4$] 3c in dichloromethane (2 ml) is stirred at room temperature for 4 days. The resulting pale yellow solid is collected by centrifugation and washed with dichloromethane (20 ml). Drying in vacuum gave the product in pure form. Yield: 99%. M.p.: 80° C. $^1$H NMR (DMSO-d$_6$): 2.18 (m, 2H), 2.58 (t, 2H), 3.86 (s, 3H), 4.25 (t, 2H), 7.71 (s, 1H), 7.77 (s, 1H), 9.09 (s, 1H). $^{13}$C NMR (DMSO-d$_6$): 132.12, 120.15, 118.69, 116.09, 44.08, 33.35, 27.87, 9.84. Microanalysis: Found (Calc.): C, 29.51 (29.50), H, 3.74 (3.71), N, 12.88 (12.90)%. IR (cm$^{-1}$): 3159, 3112 ($v_{C-H}$ aromatic), 2933 ($v_{C-H}$ aliphatic), 2324 ($v_{C≡N}$), 1721

($v_{C\equiv N}$); this compound can be dissolved in ionic liquids and used as a catalyst, the results in the hydrogenation of 1,3-cyclohexadiene are similar to those obtained in EXAMPLE 19.

Example 19

Hydrogenation of 1,3-cyclohexadiene by $PdCl_2$ in 3c $PdCl_2$ (~5 mg) is dissolved in ionic liquid 3c (1 ml), and 1,3-cyclohexadiene (1 ml) is added. The reaction is pressurized with $H_2$ to 45 atm, sealed and heated to 100° C. for 4 h which gave cyclohexene in 90% yield. The product is simply removed by decantation and no palladium is detected (based on ICP analysis).

Example 20

Comparison of Suzuki Reactions Carried Out in $[C_4mim][BF_4]$ and $[C_3CNmim][BF_4]$ (Depicted in Scheme 3)

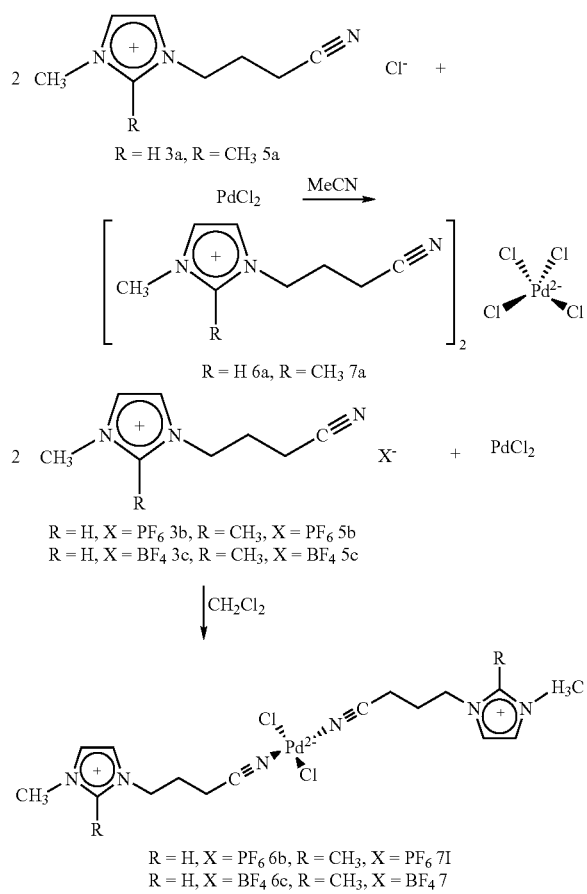

Complexes 7a, 7b, 7c are used for Suzuki coupling reaction of iodobenzene and benzeneboronic acid, as shown in scheme 2, above. Iodobenzene (2.5 mmol, 1 equiv.), benzeneboronic acid (2.75 mmol, 1.1 equiv.), $Na_2CO_3$ (560 mg, 5.28 mmol, 2.1 equiv.), palladium complex (0.03 mmol) and water (2.5 ml) are mixed with $[C_4mim][BF_4]$ (5 ml). The mixture is heated to 110° C. with vigorous stirring for 12 hours, then cooled and extracted with diethyl ether (3×15 ml). The combined organic phase is dried over $MgSO_4$ and filtered. The product, biphenyl, is obtained in 100% yield. If a nitrile ionic liquid, $[C_3CNmim][BF_4]$, is used in place of the $[C_4mim]$ $[BF_4]$, a similar yield is obtained. Significantly, using $[C_3CNmim][BF_4]$ the yields can be maintained at above 90% even after six runs of catalysis, while yields decrease rapidly for $[C_4mim][BF_4]$. Dissolving $PdCl_2$ in the $[C_3CNmim]$ $[BF_4]$ gives the same result as using complexes 6 and 7.

Examples 21 to 32 describe the dual-functionalized ionic liquids with the $[BF_3CHCH_3CH_2CN]^-$ anion.

Example 21

Synthesis of 3 (R=$CH_2CH$=$CH_2$, X=32 Br)

A mixture of 1-methylimidazole (8.21 g, 0.10 mol) and propenyl bromide (12.1 g, 0.10 mol) in methanol (50 ml) is stirred at room temperature for 5 days. The solvent is removed under reduced pressure. The resulting pale yellow viscous liquid is washed with diethyl ether (3×100 ml) and then dried in vacuum. Yield: 18.67 g, 92%; m.p.: −52.5° C.; ESI-MS ($H_2O$, m/z): positive ion, 123, $[CH_2CH$=$CH_2mim]^+$; negative ion, 80, $[Br]^{31}$; $^1H$ NMR ($D_2O$): δ 8.79 (s, 1H), 7.62 (s, 1H), 7.60 (s, 1H), 6.15 (m, 1H), 5.50 (m, 1H), 4.96 (m, 2H), 4.05 (s, 3H); $^{13}C$ NMR ($D_2O$): 136.1, 130.7, 124.5, 122.8, 121.5, 51.8, 36.3; Anal. Calcd. for $C_7H_{11}N_2Br$ (%): C, 41.40, H, 5.46, N, 13.79; Found: C, 40.41, H, 5.41, N, 13.27.

Example 22

Synthesis of 7 (R=$CH_2CH$=$CH_2$, X=Br)

A mixture of 1-allylimidazole (10.8 g, 0.10 mmol) and propenyl bromide (12.1 g, 0.10 mol) in methanol (50 ml) is stirred at room temperature for 5 days. The solvent is removed under reduced pressure. The resulting pale yellow viscous liquid is washed with diethyl ether (3×30 mL). The product is dried in vacuum for 24 h. Yield: 19.3 g, 95%; m.p.: −26.50C. ESI-MS ($H_2O$, m/z): positive ion, 149 $[DiCH_2CH$=$CH_2im]^+$; negative ion, 80 $[Br]^-$; $^1H$ NMR ($D_2O$): δ 9.20 (s, 1H). 7.85 (s, 2H), 6.20 (m, 2H), 5.55 (m, 4H), 5.10 (m, 4H); $^{13}C$ NMR ($D_2O$): 135.5, 130.5, 123.1, 122.0, 51.9; Anal. Calcd. for $C_7H_{11}N_2Br$ (%): C, 41.40, H, 5.46, N, 13.79. Found: C, 40.41, H, 5.41, N, 13.27.

Example 23

Synthesis of 10 (R=$CH_2CH_2CH_2C$≡N, X=Cl)

A mixture of trimethysilyimidazole (14.03 g, 0.10 mol) and $Cl(CH_2)_3CN$ (24.86 g, 0.24 mol) wish stirred at 80° C. for 24 h. The resulting white solid is washed with diethyl ether (3×30 mL). The product is dried in vacuum for 24 h. Yield: 22.4 g, 94%; m.p.: 100 □ C. ESI-MS ($H_2O$, m/z): positive ion, 203 $[Di(CH_2)_3C$≡$Nim]^+$; negative ion, 35, 37 $[Cl]^-$; $^1H$ NMR ($D_2O$): δ 8.56 (s, 1H), 7.52 (s, 2H), 4.48 (t, 4H, $^3J$(H, H)=7.15 Hz), 2.66 (m, 4H), 2.35 (t, 4H, $^3J$(H, H)=7.15 Hz); $^{13}C$ NMR ($D_2O$): 137.10, 123.4, 119.2, 48.3, 29.3, 25.1; IR ($cm^{-1}$): 3166, 3075, 2939, 2895, 2839, 2241, 1781, 1669, 1570, 1559; Anal. Calcd for $C_{11}H_{15}ClN_4$ (%): C, 55.35, H, 6.33, N, 23.47. Found: C, 54.98, H, 6.08, N, 23.55.

Example 24

Synthesis of 11 ($R_1$=$CH_2CH_2CH_2CH_3$, $R_2$=$CH_3$)

A mixture of 1 (1.0 g, 5.71 mmol) and 2 (1.0 g, 5.71 mmol) is stirred in acetone at room temperature for 24 h. The resulting suspension is filtered and the filtrate dried in vacuum. The resulting ionic liquid is purified by washing with diethyl ether, and the solvents removed in vacuum. Yield: 1.32 g, 84%. Pale yellow liquid, m.p.: −84.5° C.; ESI-MS (H$_2$O, m/z): positive ion, 139, [C$_4$mim]$^+$; negative ion, 136, [CH$_3$(BF$_3$)CHCH$_2$CN]$^-$; $^1$H NMR (d6-acetone): δ 8.28 (s, 1H), 7.16 (s, 1H), 7.11 (s, 1H), 4.45 (t, $^3$J(H, H)=7.15 Hz, 2H), 3.85 (s, 3H), 2.35-1.94 (m, 4H), 1.92-1.85 (m, 2H), 1.32 (t, 3H, $^3$J(H, H)=6.98 Hz), 1.20 (m, 2H), 0.89 (d, 3H, $^3$J(H, H)=7.3 Hz), 0.56 (m, 1H); $^{13}$C NMR (d6-acetone): δ 136.8, 126.3, 124.5, 121.7, 49.0, 35.7, 31.9, 29.2, 20.6, 19.6, 15.5, 13.0; $^{19}$F NMR (d6-acetone): −149.8 (m); IR (cm$^{-1}$): 3154, 3117, 2962, 2872, 2239, 1574; Anal. Calcd. for C$_{12}$H$_{21}$BF$_3$N$_3$ (%): C, 52.39, H, 7.69, N, 15.27. Found: C, 52.38, H, 7.41, N, 15.51.

Example 25

Synthesis of 12 (R$_1$=CH$_2$CH=CH$_2$, R$_2$=CH$_3$)

The same method is used as in the synthesis of 11 except 3 (1.16 g, 5.71 mmol) is used in place of 2. Yield: 1.30 g, 88%. Pale yellow liquid, m. p.: −89.2° C.; ESI-MS (H$_2$O, m/z): positive ion, 123, [CH$_2$CH=CH$_2$mim]$^+$; negative ion, 136, [CH$_3$(BF$_3$)CHCH$_2$CN]$^-$; $^1$H NMR (d6-acetone): δ 8.89 (s, 1H), 7.67 (s, 1H), 7.66 (s, 1H), 6.07 (m, 1H), 5.58 (m, 1H), 4.92 (m, 1H), 4.61 (s, 3H), 3.95 (s, 2H), 2.34 (dd, 1H, $^2$J(H, H)=−17.1 Hz, $^3$J(H, H)=4.3 Hz), 1.96 (dd, 1H, $^2$J(H, H)=−17.1, $^3$J(H, H)=10.7 Hz), 0.87 (d, 3H, $^3$J(H, H)=7.3 Hz), 0.54 (m, 1H); $^{13}$C NMR (d6-acetone): 139.01, 136.7, 124.89, 122.7, 121.5, 121.7, 51.3, 35.9, 28.5, 20.2, 14.8; $^{19}$F NMR (d6-acetone): −147.4 (m); IR (cm$^{-1}$): 3151, 3114, 1647, 2943, 2865, 2238, 1708, 1647, 1574; Anal. Calcd. for C$_{11}$H$_{17}$BF$_3$N$_3$ (%): C, 51.00, H, 6.61, N, 16.22; Found: C, 51.21, H, 6.45, N, 16.17.

Example 26

Synthesis of 13 (R$_1$=CH$_2$C≡CH, R$_2$=CH$_3$)

The same method is used as in the synthesis of 11 except 4 (1.15 g, 5.71 mmol) is used in place of 2. Yield: 1.20 g, 82%. Pale yellow liquid, m.p.: −80.4° C.; ESI-MS (H$_2$O, m/z): positive ion, 121, [CH$_2$C≡CHmim]$^+$; negative ion, 136, [CH$_3$(BF$_3$)CHCH$_2$CN]$^-$; $^1$H NMR (d6-acetone): δ 9.49 (s, 1H). 7.87 (s, 1H), 7.58 (s, 1H), 5.40 (d, 2H, $^4$J(H, H)=2.80 Hz), 4.37 (s, 3H), 3.21 (d, 4H, $^4$J(H, H)=2.80 Hz); 2.36 (dd, 1H, $^2$J(H, H)=−17.1 Hz, $^3$J(H, H)=4.3 Hz), 1.91 (dd, 1H, $^2$J(H, H)=−17.1, $^3$J(H, H)=10.7 Hz), 0.89 (d, 3H, $^3$J(H, H)=7.3 Hz), 0.54 (m, 1H); $^{13}$C NMR (acetone): δ 137.2, 124.2, 122.2, 121.2, 78.2, 75.2, 35.9, 29.3, 28.7, 20.5, 15.1; $^{19}$F NMR (d6-acetone): −148.8 (m); IR (cm$^{-1}$): 3252, 3156, 3116, 2960, 2867, 2238, 2131, 1697, 1625, 1576, 1459, 1425; Anal. Calcd. for C$_{11}$H$_{15}$BF$_3$N$_3$ (%): C, 51.40, H, 5.88, N, 16.35. Found: C, 51.21, H, 5.75, N, 16.32.

Example 27

Synthesis of 14 (R$_1$=CH$_2$CH$_2$CH$_2$COOH, R$_2$=CH$_3$)

The same method is used as synthesis of 11 except 5 (1.17 g, 5.71 mmol) is used in place of 2. Yield: 1.53 g, 88%. Colourless liquid, m.p.: −58.6° C.; ESI-MS (H$_2$O, m/z): positive ion, 169, [CH$_2$CH$_2$CH$_2$COOHmim]$^+$; negative ion, 136, [CH$_3$(BF$_3$)CHCH$_2$CN]$^-$; $^1$H NMR (d6-acetone): δ 10.33 (br, 1H), 9.01 (s, 1H), 7.75 (s, 1H), 7.72 (s, 1H), 4.35 (t, 2H, $^3$J(H, H)=7.05 Hz), 4.00 (s, 3H), 2.17 (t, 2H, $^3$J(H,H)=7.05), 2.39-1.96 (m, 2H), 0.89 (d, 3H, $^3$J(H, H)=7.3 Hz), 0.55 (m, 1H); $^{13}$C NMR (d6-acetone): δ=173.7, 136.0, 124.6, 121.1, 48.46, 35.1, 30.9, 28.9, 20.5, 15.1; $^{19}$F NMR (d6-acetone): −148.8 (m); IR (cm$^{-1}$): 3155, 3117, 2943, 2867, 2238, 1728, 1566, 1460; Anal. Calcd. for C$_{12}$H$_{19}$BF$_3$N$_3$O$_2$ (%): C, 47.24, H, 6.28, N, 13.77; Found: C, 471.21, H, 6.75, N, 13.32.

Example 28

Synthesis of 15 (R$_1$=CH$_2$CH$_2$CH$_2$C≡N, R$_2$=CH$_3$)

The same method is used as in the synthesis of 11 except 6 (1.06 g, 5.71 mmol) is used in place of 2. Yield: 1.39 g, 85%. Pale yellow liquid, m.p.: −76.6° C.; ESI-MS (H$_2$O, m/z): positive ion, 150 [CH$_2$CH$_2$CH$_2$CNmim]$^+$; negative ion, 136, [CH$_3$(BF$_3$)CHCH$_2$CN]$^-$; $^1$H NMR (d6-acetone): δ=8.75 (s, 1H), 7.44 (s, 1H), 7.39 (s, 1H), 4.45 (t, 2H, $^3$J(H, H)=7.15 Hz), 4.00 (s, 3H), 2.64 (t, 2H, $^3$J(H, H)=7.15 Hz), 2.31 (t, 2H, $^1$J(H, H)=7.14 Hz), 2.30 (m, 1H), 1.98 (dd, 1H, $^2$J(H, H)=−17.1, $^3$J(H, H)=10.7 Hz), 0.87 (d, 3H, $^3$J(H, H)=7.3 Hz), 0.55 (m, 1H); $^{13}$C NMR (d6-acetone): δ 134.11, 130.49, 120.0, 121.5, 116.1, 48.0, 30.8, 28.9, 25.9, 20.5, 13.6, 9.8; $^{19}$F NMR (d6-acetone): −148.8 (m); IR (cm$^{-1}$): 3156, 3116, 2960, 2866, 2239, 1631, 1575, 1566, 1459, 1425; Anal. Calcd. for C$_{12}$H$_{18}$BF$_3$N$_4$ (%): C, 50.38, H, 6.34, N, 19.58; Found: C, 50.21, H, 6.45, N, 19.32.

Example 29

Synthesis of 16 (R$_1$=R$_2$=CH$_2$CH=CH$_2$)

The same method is used as in the synthesis of 11 except 7 (1.31 g, 5.71 mmol) is used in place of 2. Yield: 1.43 g, 88%. Pale yellow liquid, m.p.: −87.3° C.; ESI-MS (H$_2$O, m/z): positive ion, 149 [DiCH$_2$CH=$_2$im]$^+$; negative ion, 136, [CH$_3$(BF$_3$)CHCH$_2$CN]$^-$; $^1$H NMR (d6-acetone): δ 9.25 (s, 1H). 7.86 (s, 2H), 6.11 (m, 2H), 5.45-5.35 (m, 4H), 4.99 (m, 4H), 2.31 (dd, 1H, $^2$J(H, H)=−17.1 Hz, $^3$J(H, H)=4.3 Hz), 1.95 (dd, 1H, $^2$J(H, H)=−17.1, $^3$J(H, H)=10.7 Hz), 1.20 (m, 2H), 0.88 (d, 3H, $^3$J(H, H)=7.3 Hz), 0.56 (m, 1H); $^{13}$C NMR (d6-acetone): δ 136.0, 131.7, 122.07, 121.7, 120.8, 51.4, 29.4, 20.6, 15.3; $^{19}$F NMR (d6-acetone): −149.8 (m); R (cm$^{-1}$): 3143, 3087, 2943, 2866, 2238, 1646, 1562, 1451, 1424; Anal. Calcd. for C$_{13}$H$_{19}$BF$_3$N$_3$(%): C, 54.76, H, 6.72, N, 14.74. Found: C, 54.21, H, 6.85, N, 14.41.

Example 30

Synthesis of 17 (R$_1$=R$_2$=CH$_2$C≡CH)

The same method is used as in the synthesis of 11 except 8 (1.03 g, 5.71 mmol) is used in place of 2. Yield: 1.38 g, 86%. Pale yellow liquid, m.p.: −55.1° C.; ESI-MS (H$_2$O, m/z): positive ion, 145 [DiCH$_2$C≡CHim]$^+$; negative ion, 136, [CH$_3$(BF$_3$)CHCH$_2$CN]$^-$; $^1$H NMR (D$_2$O): δ=9.36 (s, 1H), 7.90 (s, 2H), 5.97 (d, 4H, $^4$J(H, H)=4.0 Hz), 3.36 (t, 2H, $^4$J(H, H)=4.0 Hz), 2.35 (dd, 1H, $^2$J(H, H)=−17.1 Hz, $^3$J(H, H)=4.3 Hz), 1.94 (dd, 1H, $^2$J(H, H)=−17.1, $^3$J(H, H)=10.7 Hz), 0.89

(d, 3H, $^3$J(H, H)=7.3 Hz), 0.56 (m, 1H); $^{13}$C NMR (D$_2$O): δ 138.9, 125.7, 121.7, 81.1, 74.8, 42.5, 29.2, 20.5, 15.4; $^{19}$F NMR (d6-acetone): −149.8 (m); IR (cm$^{-1}$): 3255, 3145, 2944, 2867, 2239, 2131, 1559, 1445; Anal. Calcd. for C$_{13}$H$_{15}$BF$_3$N$_3$(%): C, 55.55, H, 5.38, N, 14.95; Found: C, 55.21, H, 5.45, N, 14.69.

Example 31

Synthesis of 18 (R$_1$=R$_2$=CH$_2$CH$_2$CH$_2$COOH)

The same method is used as in the synthesis of 11 except 9 (1.58 g, 5.71 mmol) is used in place of 2 as waxy solid. Yield: 1.83 g, 85%. ESI-MS (H$_2$O, m/z): positive ion, 241, [DiCH$_2$CH$_2$CH$_2$COOHim]$^+$; negative ion, 136, [CH$_3$(BF$_3$)CHCH$_2$CN]$^-$; $^1$H NMR (d6-acetone): δ8.76 (s, 1H), 7.44 (s, 2H), 4.08 (t, 4H, $^3$J(H, H)=7.05 Hz), 2.38-2.30 (m, 1H) 2.37 (t, 4H, $^3$J(H, H)=7.05 Hz), 2.08 (m, 4H), 1.97 (dd, 1H, $^2$J(H, H)=−17.1, $^3$J(H, H)=10.7 Hz), 1.21 (m, 2H), 0.90 (d, 3H, $^3$J(H, H)=7.3 Hz), 0.59 (m, 1H); $^{13}$C NMR (d6-acetone): δ 179.7, 138.5, 125.5, 121.8, 51.6, 33.1, 28.4, 27.5, 20.3, 14.9; $^{19}$F NMR (d6-acetone): −149.8 (m); IR (cm$^{-1}$): 3607, 3454, 3151, 2946, 2873, 2246, 1727, 1651, 1565, 1460, 1421, 1308; Anal. Calcd. for C$_{15}$H$_{23}$BF$_3$N$_3$O$_4$(%): C, 47.77, H, 6.15, N, 11.14. Found: C, 47.35, H, 6.25, N, 11.38.

Example 32

Synthesis of 19 (R$_1$=R$_2$=CH$_2$CH$_2$CH$_2$C≡N)

The same method is used as in the synthesis of 11 except 10 (1.39 g, 5.71 mmol) is used in place of 2. Yield: 1.68 g, 87%.

Colourless liquid, m.p.: −69.8° C.; ESI-MS (H$_2$O, m/z): positive ion, 203 [Di(CH$_2$)$_3$C≡Nim]$^+$; negative ion, 136, [CH$_3$(BF$_3$)CHCH$_2$CN]$^-$; $^1$H NMR (d6-acetone): δ 9.30 (s, 1H), 7.83 (s, 2H), 4.46 (t, 4H, $^3$J(H, H)=7.10 Hz), 2.66 (m, 4H), 2.32 (t, 4H, $^3$J(H, H)=7.00 Hz), 2.34 (dd, 1H, $^2$J(H, H)=−17.1 Hz, $^3$J(H, H)=4.3 Hz), 1.99 (dd, 1H, $^2$J(H, H)=−17.1Hz, $^3$J(H, H)=10.7 Hz), 0.91 (d, 3H, $^3$J(H, H)=7.3 Hz), 0.58 (m, 1H); $^{13}$C NMR (d6-acetone): 137.0, 123.4, 121.9, 119.2, 48.3, 29.3, 29.1, 25.1, 20.6, 13.6; $^{19}$F NMR (d6-acetone): −148.8 (m); IR (cm$^{-1}$): 3148, 3117, 2967, 2247, 1567, 1461, 1425; Anal. Calcd. for C$_{15}$H$_{21}$BF$_3$N$_5$(%): C, 53.12, H, 6.24, N, 20.65. Found: C, 52.97, H, 6.25, N, 20.34.

The stability of the nitrile-functionalised anion towards catalytic hydrogenation is tested by pressurising a solution of K[CH$_3$CH(BF$_3$)CH$_2$CN] (8 mg) and RuCl$_2$(PMe$_3$)$_4$ (1 mg) in acetone (0.4 ml) with H$_2$ (40 bar) at 35° C. No reduction was observed even after 48 hours.

Example 33

Melting point data

| Entry | Cation | Anion | Melting Point (° C.) |
|---|---|---|---|
| 1a | [CCNmim) | Cl | 170 |
| 1b | [CCNmim] | PF$_6$ | 78 |
| 1c | [CCNmim] | BF$_4$ | 35 |
| 2a | [C$_2$CNmim] | Cl | 50 |
| 2b | [C$_2$CNmim] | PF$_6$ | 35 |
| 2c | [C$_2$CNmim] | BF$_4$ | 20 |
| 3a | [C$_3$CNmim] | Cl | 80 |
| 3b | [C$_3$CNmim] | PF$_6$ | 75 |
| 3c | [C$_3$CNmim] | BF$_4$ | −71.9 |
| 4a | [C$_4$CNmim] | Cl | 32 |
| 4b | [C$_4$CNmim] | PF$_6$ | −60.3 |
| 4c | [C$_4$CNmim] | BF$_4$ | −74.5 |
| 5a | [C$_4$CNdimim] | Cl | 105 |
| 5b | [C$_4$CNdimim] | PF$_6$ | 85 |
| 5c | [C$_4$CNdimim] | BF$_4$ | 40 |

Example 34

Density, viscosity and solubility in common solvents

| Entry | Ionic liquids | Density (g·ml$^{-1}$) | Viscosity (mpa·s) | Solubility in common solvents | | | | |
|---|---|---|---|---|---|---|---|---|
| | | | | H$_2$O | Et$_2$O | EtOH | Acetone | Hexane |
| 1 | [C$_2$CNmim][Cl] | 2.67 | 2856 | miscible | immiscible | miscible | immiscible | immiscible |
| 2 | [C$_2$CNmim][BF$_4$] | 2.15 | 65.5 | miscible | immiscible | miscible | miscible | immiscible |
| 3 | [C$_3$CNmim][BF$_4$] | 1.87 | 230 | miscible | immiscible | immiscible | miscible | immiscible |
| 4 | [C$_4$CNmim][Cl] | 1.61 | 5222 | miscible | immiscible | miscible | immiscible | immiscible |
| 5 | [C$_4$CNmim][PF$_6$] | 1.99 | 2181 | partly miscible | immiscible | immiscible | miscible | immiscible |
| 6 | [C$_4$CNmim][BF$_4$] | 1.71 | 552.9 | miscible | immiscible | immiscible | miscible | immiscible |
| 7 | [C$_4$mim][PF$_6$] | 1.37 | 320.3 | partly miscible | immiscible | partly miscible | miscible | immiscible |
| 8 | [C$_4$mim][BF$_4$] | 1.14 | 115.2 | miscible | immiscible | immiscible | miscible | immiscible |

Example 35

Comparison of the melting point and viscosity data of the DF-ILs with tetrafluoroborate counterparts.

| Ionic liquids$^a$ | Melting Point (° C.) | Viscosity (cp, 20° C.) |
|---|---|---|
| 11 | −84.5 | 101.4 |
| [C$_4$mim][BF$_4$]$^2$ | −81.0 | 115.2 |
| 12 | −89.2 | 25.8 |
| [CC≡Cmim][BF$_4$]$^{5b}$ | −81.1 | 6110 |
| 13 | −80.4 | 175.1 |
| 14 | −58.6 | 3047 |
| [C$_3$COOHmim][BF$_4$] | −58.0 | 4415 |
| 15 | −76.6 | 107.5 |

-continued

Comparison of the melting point and viscosity data of the DF-ILs with tetrafluoroborate counterparts.

| Ionic liquids[a] | Melting Point (° C.) | Viscosity (cp, 20° C.) |
|---|---|---|
| [C$_3$CNmim][BF$_4$][4] | −71.9 | 230.0 |
| 16 | −87.3 | 56.8 |
| 17 | −55.1 | 1797 |
| [DiCC═Cmim][BF$_4$][3b] | 67.0 | — |
| 18 | 38.0 | — |
| 19 | −69.8 | 402.4 |

[a][C$_4$mim][BF$_4$]: 1-methyl-3-butylimidazolium tetrafluoroborate; [CC═Cmim][BF$_4$]: 1-methyl-3-allylimidazolium tetrafluoroborate; [DiCC═Cmim][BF$_4$]: 1,3-di-akylimidazolium tetrafluoroborate; [C$_3$COOHmim][BF$_4$]: 1-methyl-3-proylcarboxylimidazolium tetrafluoroborate.

What is claimed is:

1. A compound having the general formula,

K$^+$A$^-$, in which K$^+$ is a 5- or 6-membered heterocyclic ring having 1-3 hetero atoms, which can be independently N, S, or O, with the proviso that at least one of the hetero atoms must be a quaternized nitrogen atom;

the heterocyclic ring having up to 5 substituents independently chosen from:
  (i) H;
  (ii) halogen;
  (iii) C$_1$ to C$_{12}$ alkyl, which is unsubstituted or partially or fully substituted by at least one substituent selected from the group consisting of F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$ or C$_n$F$_{(2n+1-x)}$H$_x$ where 1<n<6 and 0<x<13;
  (iv) phenyl, which is unsubstituted or partially or fully substituted by at least one substituent selected from the group consisting of F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$ or C$_n$F$_{(2n+1-x)}$H$_x$ where 1<n<6 and 0<x≦13; and,
  (v) —R'CN where R' is C$_1$ to C$_{12}$ alkyl;
wherein the quaternized nitrogen atom of the heterocyclic ring is substituted by the substituent of (v); and,
A$^-$ is [BF$_3$RCN]$^-$ wherein R is C$_1$ to C$_{12}$ alkyl.

2. The compound of claim 1 wherein A$^-$ is [BF$_3$CHCH$_3$CH$_2$CN]$^-$.

3. The compound of 1 or 2 complexed with a compound selected from the group consisting of PdCl$_2$, PtCl$_2$, RuCl$_3$, RhCl$_3$, or [Ru(arene)Cl$_2$]$_2$.

4. The compound of claim 1 wherein the C$_1$ to C$_{12}$ alkyl of (iii) on the heterocyclic ring is partially or fully substituted by a moiety selected from the group consisting of F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$ or C$_n$F$_{(2n+1-x)}$H$_x$, where 1<n<6 and 0<x<13.

5. The compound of claim 1 wherein the phenyl of (iv) on the heterocyclic ring is partially or fully substituted by at least one moiety selected from the group consisting of F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$, and C$_n$F$_{(2n+1-x)}$H$_x$, where 1<n<6 and 0<x≦13.

6. The compound of claim 1 wherein the C$_1$ to C$_{12}$ alkyl of (iii) is partially or fully substituted by at least one moiety selected from the group consisting F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$ or C$_n$F$_{(2n+1-x)}$H$_x$ where 1<n<6 and 0<x<13, and the phenyl of (iv) is partially or fully substituted by at least one moiety selected from the group consisting of F, Cl, N(C$_n$F$_{(2n+1-x)}$H$_x$)$_2$, O(C$_n$F$_{(2n+1-x)}$H$_x$), SO$_2$(C$_n$F$_{(2n+1-x)}$H$_x$)$_2$ or C$_n$F$_{(2n+1-x)}$H$_x$ where 1<n<6 and 0<x<13.

* * * * *